US00PP31945P3

(12) United States Plant Patent
Post

(10) Patent No.: US PP31,945 P3
(45) Date of Patent: Jul. 7, 2020

(54) ***CHRYSANTHEMUM* PLANT NAMED 'DLFYIN2'**

(50) Latin Name: ***Chrysanthemum* X *morifolium***
Varietal Denomination: DLFYIN2

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 16/501,359

(22) Filed: Mar. 29, 2019

(65) Prior Publication Data

US 2019/0307046 P1 Oct. 3, 2019

Related U.S. Application Data

(60) Provisional application No. 62/761,600, filed on Mar. 30, 2018.

(51) Int. Cl.
*A01H 5/02* (2018.01)
*A01H 6/14* (2018.01)

(52) U.S. Cl.
USPC ..... Plt./295
CPC ..... *A01H 6/1424* (2018.05)

(58) Field of Classification Search
USPC ..... Plt./295
See application file for complete search history.

*Primary Examiner* — Anne Marie Grunberg
(74) *Attorney, Agent, or Firm* — C. A. Whealy

(57) ABSTRACT

A new and distinct cultivar of *Chrysanthemum* plant named 'DLFYIN2', characterized by its upright and relatively compact plant habit; vigorous growth habit; dark green-colored leaves; uniform and freely flowering habit; strong upright flowering stems with numerous inflorescences; small single-type inflorescences with yellow-colored ray florets and dark brown-colored disc florets; and excellent postproduction longevity.

2 Drawing Sheets

Botanical designation: *Chrysanthemum* X *morifolium.*
Cultivar denomination: 'DLFYIN2'.

CROSS-REFERENCED TO CLOSELY RELATED APPLICATIONS

Title: Varieties of *Chrysanthemum* Plants
Applicant: Arie Gerard Post
Provisional application Ser. No. 62/761,600
Filed: Mar. 30, 2018

BACKGROUND OF THE INVENTION

The present invention relates to a new and distinct cultivar of *Chrysanthemum* plant, botanically known as *Chrysanthemum* X *morifolium,* commercially grown as a cut flower and hereinafter referred to by the name 'DLFYIN2'.

The new *Chrysanthemum* plant is a product of a planned breeding program conducted by the Inventor in Maasdijk, The Netherlands. The objective of the breeding program is to create new freely-flowering cut *Chrysanthemum* plants with attractive inflorescences, strong flowering stems and excellent postproduction longevity.

The new *Chrysanthemum* plant is a naturally-occurring whole plant mutation of *Chrysanthemum* X *morifolium* 'DLFYIN1', not patented. The new *Chrysanthemum* plant was discovered and selected by the Inventor as a single plant from within a population of plants in a controlled greenhouse environment in Maasdijk, The Netherlands on Nov. 9, 2015.

Asexual reproduction of the new *Chrysanthemum* plant by vegetative terminal cuttings since Nov. 9, 2015 has shown that the unique features of this new *Chrysanthemum* plant are stable and reproduced true to type in successive generations of asexual reproduction. The instant plant was first asexually propagated in Maasdijk, The Netherlands.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFYIN2'. These characteristics in combination distinguish 'DLFYIN2' as a new and distinct *Chrysanthemum* plant:

1. Upright and relatively compact plant habit; vigorous growth habit.
2. Dark green-colored leaves.
3. Uniform and freely flowering habit.
4. Strong upright flowering stems with numerous inflorescences.
5. Small single-type inflorescences with yellow-colored ray florets and dark brown-colored disc florets.
6. Excellent postproduction longevity.

Plants of the new *Chrysanthemum* differ primarily from plants of the mutation parent, 'DLFYIN1', in ray floret color as plants of the new *Chrysanthemum* have yellow-colored ray florets whereas plants of 'DLFYIN1' have white-colored ray florets.

Plants of the new *Chrysanthemum* can be compared to plants of *Chrysanthemum* X *morifolium* 'DLFPRO2', not patented. In side-by-side comparisons plants of the new *Chrysanthemum* differ from plants of 'DLFPRO2' in the following characteristics:

1. Ray florets of plants of the new *Chrysanthemum* are lighter yellow in color than ray florets of plants of 'DLFPRO2'.
2. Disc florets of plants of the new *Chrysanthemum* are dark brown in color whereas disc florets of plants of 'DLFPRO2' are green in color.

Plants of the new *Chrysanthemum* can also be compared to plants of *Chrysanthemum* X *morifolium* 'Delaviso', not patented. In side-by-side comparisons plants of the new *Chrysanthemum* differ from plants of 'Delaviso' in the following characteristics:

1. Ray florets of plants of the new *Chrysanthemum* are lighter yellow in color than ray florets of plants of 'Delaviso'.
2. Disc florets of plants of the new *Chrysanthemum* are dark brown in color whereas disc florets of plants of 'Delaviso' are green in color.

BRIEF DESCRIPTION OF THE PHOTOGRAPHS

The accompanying colored photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'DLFYIN2' grown as a spray-type.

The photograph on the second sheet comprises close-up views of the lower (top of the photographic sheet) and upper surfaces (bottom of the photographic sheet) of typical inflorescences and leaves of 'DLFYIN2'.

DETAILED BOTANICAL DESCRIPTION

The aforementioned photographs and following observations and measurements describe plants grown during the winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 22° C., night temperatures ranged from 20° C. to 25° C. and light levels averaged 8 klux. Plants were grown as single-stem plants and were eight weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFYIN2'.

Parentage: Naturally-occurring whole plant mutation of *Chrysanthemum* X *morifolium* 'DLFYIN1', not patented.

Propagation:

*Type.*—Terminal vegetative cuttings.

*Time to initiate roots, summer.*—About six days at temperatures about 24° C.

*Time to initiate roots, winter.*—About eight days at temperatures about 22° C.

*Time to produce a rooted young plant, summer.*—About twelve days at temperatures about 24° C.

*Time to produce a rooted young plant, winter.*—About two weeks at temperatures about 22° C.

*Root description.*—Fine, fibrous; typically creamy white in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous single daisy-type cut flower that is typically grown as a single stem spray-type; upright plant habit; vigorous growth habit and moderate to rapid growth rate.

*Plant height, soil level to top of foliar plane.*—About 73 cm.

*Plant height, soil level to top of inflorescence plane.*—About 78.3 cm.

*Plant (spray) diameter.*—About 13.5 cm.

*Flowering stem length.*—About 70.4 cm.

*Flowering stem diameter.*—About 5.5 mm.

*Flowering stem internode length.*—About 1.8 cm.

*Flowering stem strength.*—Strong.

*Flowering stem aspect.*—Erect.

*Flowering stem texture and luster.*—Moderately pubescent; slightly glossy.

*Flowering stem color, developing.*—Close to 144B, at the internodes, close to 146C.

*Flowering stem color, developed.*—Close to 146B and 146C.

*Leaf description.*—Arrangement: Alternate; simple. Length: About 7.6 cm. Width: About 4.3 cm. Shape: Ovate to oblong. Apex: Short apiculate. Base: Narrow attenuate. Margin: Palmately lobed, coarsely serrate to crenate; sinuses convergent and medium to deep in depth. Texture and luster, upper surface: Moderately pubescent, not rugose; moderately velvety; very slightly glossy. Texture and luster, upper surface: Moderately pubescent, prominent venation; slightly velvety; matte. Venation pattern: Pinnate, reticulate. Color: Developing leaves, upper surface: Close to 137B. Developing leaves, lower surface: Close to 147B. Fully developed leaves, upper surface: Close to NN137A; venation, close to 143B. Fully developed leaves, lower surface: Close to 147B; venation, close to 146C. Petioles: Length: About 1.5 cm. Diameter: About 2 mm by 2.5 mm. Strength: Moderately strong. Texture and luster, upper and lower surfaces: Moderately to densely pubescent; moderately glossy. Color, upper surface: Close to 146C; edges, close to 147A. Color, lower surface: Close to 147C; edges, close to NN137B. Stipules: Quantity and appearance: Two leafy stipules, opposite, at the petiole attachment to the stem. Length: About 1 cm. Width: About 1.4 cm. Shape: Flabellate. Texture and luster, upper surface: Moderately pubescent; very slightly glossy. Texture and luster, upper surface: Moderately pubescent; matte. Color, upper surface: Close to NN137A. Color, lower surface: Close to 147B.

Inflorescence description:

*Appearance.*—Single-type (daisy) inflorescence form with elliptic to obovate-shaped ray florets and tubular disc florets; inflorescences borne perpendicular to peduncles and face mostly upright to slightly outwardly; ray and disc florets develop acropetally on a capitulum.

*Fragrance.*—Faintly fragrant.

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 45 days later when grown as a spray-type.

*Postproduction longevity.*—Good postproduction longevity; in an interior environment, inflorescences and foliage will maintain good color and substance for about two weeks; inflorescences persistent.

*Quantity of inflorescences.*—Freely flowering habit; when grown as a spray-type, about 18 inflorescences develop per flowering stem.

*Inflorescence size.*—Diameter: About 3.1 cm. Depth (height): About 1.2 cm. Disc diameter: About 1.2 cm.

*Receptacles.*—Height: About 4 mm. Diameter: About 4.5 mm. Shape: Broadly ovoid. Color: Close to 145B.

*Inflorescence buds.*—Height: About 7 mm. Diameter: About 1.2 cm. Shape: Broadly oblong to flattened globular. Texture and luster: Distally, smooth and glabrous; proximally, sparsely pubescent; very slightly glossy. Color: Distally, 5C and 146B (immature ray florets); proximally, close to 137B.

*Ray florets.*—Quantity and arrangement: About 23 arranged in about two whorls. Length: About 1.4 cm. Width: About 7 mm. Shape: Elliptic to obovate; slightly convex, slightly carinate, slightly curved downward. Apex: Shallowly emarginate to shallowly praemorse. Base: Attenuate. Margin: Entire; not undulate. Aspect: Initially upright to about 65° from vertical. Texture and luster, upper surface: Smooth, glabrous; moderately velvety; matte. Texture and luster, lower surface: Smooth, glabrous; moderately velvety; moderately glossy. Color: When opening, upper surface: Close to 5A. When opening, lower surface: Close to 5C. Fully opened, upper surface: Close to 4A, towards the base, close to 3A; venation, similar to lamina; color does not change with development. Fully opened, lower surface: Close to 4C; venation, similar to lamina; color does not change with development.

*Disc florets.*—Quantity and arrangement: About 200 spirally arranged in about eight whorls at the center of the receptacle. Length: About 5 mm. Diameter: About 1.25 mm. Shape: Lower 75% fused into a tube; upper 25% free. Apex: Acute. Margin: Entire. Texture and luster, inner and outer surfaces: Smooth, glabrous; glossy. Color, when opening, inner and outer surfaces: Apex: Close to N144D; tipped with close to 200A. Mid-section: Close to 13C. Base: Close to N144D. Color, fully opened, inner and outer surfaces: Apex: Close to N144C; tipped with close to 200A. Mid-section: Close to 12B. Base: Close to 145C.

*Involucral bracts.*—Quantity and arrangement: About 26 arranged in two whorls. Length: About 7 mm. Width: About 3 mm. Shape: Ovate. Apex: Obtuse. Base: Cuneate. Margin: Entire. Texture and luster, upper surface: Smooth, glabrous; moderately glossy. Texture and luster, lower surface: Moderately pubescent; matte. Color, upper surface: Close to 137B; margins, translucent, and close to 157D; apices, close to N199A. Color, lower surface: Close to NN137C; margins, translucent, close to 157D; apices, close to N199A.

*Peduncles.*—Length, terminal peduncle: About 5.1 cm. Diameter, terminal peduncle: About 1.5 mm. Length, third peduncle: About 7.3 cm. Diameter, terminal peduncle: About 2 mm. Strength: Strong. Aspect, terminal peduncle: Mostly upright. Aspect, third peduncle: About 30° from the flowering stem axis. Texture and luster: Moderately pubescent; matte. Color: Close to between 143A and 144A.

*Reproductive organs.*—Androecium: Present on disc florets only. Quantity: About five per floret. Filament length: About 2 mm. Filament color: Close to 150D. Anther size: About 0.5 mm by 1.5 mm. Anther shape: Narrowly oblong. Anther color: Close to 13A. Pollen amount: None observed. Gynoecium: Present on both ray and disc florets. Quantity: One per floret. Pistil length: About 4 mm. Style length: About 3 mm. Style color: Close to N144D. Stigma diameter: About 1 mm. Stigma shape: Cleft, decurrent. Stigma color: Close to 154C. Ovary color: Close to 145D.

*Seeds and fruits.*—To date, seed and fruit production have not been observed on plants of the new *Chrysanthemum.*

Pathogen & pest resistance: Plants of the new *Chrysanthemum* have been observed to be resistant to *Fusarium* Wilt (*Fusarium oxysporum f.* sp. *chrysanthemi*). To date, resistance to pests and other pathogens common to *Chrysanthemum* plants has not been observed on plants of the new *Chrysanthemum* grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFYIN2' as illustrated and described.

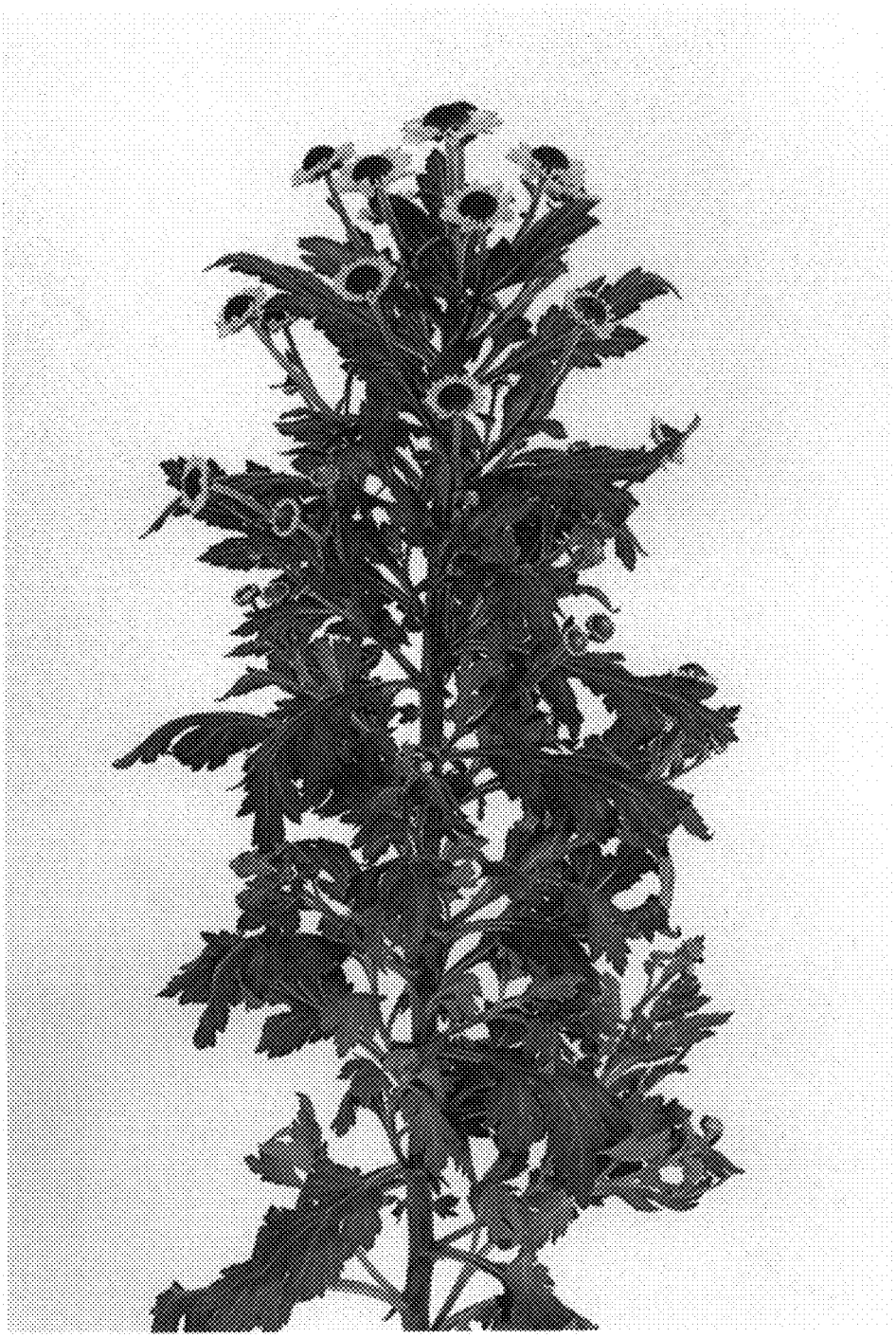

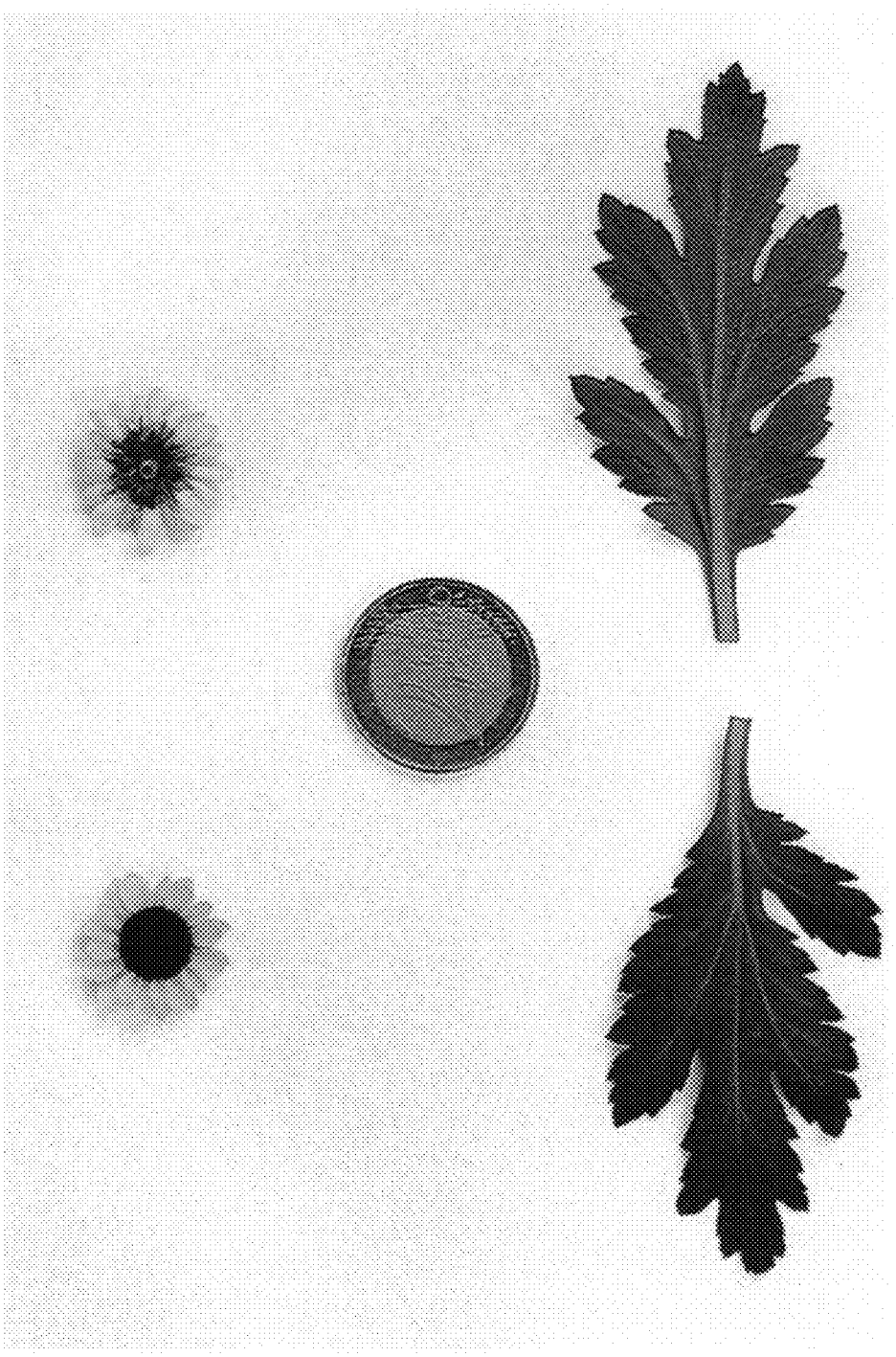

* * * * *